US00PP30399P2

(12) United States Plant Patent
van Langen

(10) Patent No.: US PP30,399 P2
(45) Date of Patent: Apr. 16, 2019

(54) ***HAWORTHIA* PLANT NAMED 'AMIHAW1801'**

(50) Latin Name: *Haworthia pentagona*
Varietal Denomination: AMIHAW1801

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/932,625

(22) Filed: Mar. 27, 2018

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Haworthia* plant named 'AMIHAW1801', which is characterized by a fast rate of growth, succulent foliage that is held upright in a spirally-arranged rosette, large, broadly deltoid foliage with coarsely dentate margins, and dark green foliage which is tolerant of high light levels. The new variety has shown to be uniform and stable in the resulting generations from asexual propagation.

4 Drawing Sheets

Latin name of the genus and species: The Latin name of the genus and species of the novel variety disclosed herein is *Haworthia pentagona.*

Variety denomination: The inventive variety of *Haworthia* plant disclosed herein has been given the variety denomination 'AMIHAW1801'.

BACKGROUND OF THE INVENTION

Parentage: 'AMIHAW1801' originated as a naturally occurring, whole-plant mutation of an unnamed *Haworthia pentagona* plant (not patented). In September of 2013 the inventor discovered the mutation at a commercial greenhouse in Heerhugowaard, the Netherlands, growing amongst a crop of the species *Haworthia pentagona*. The mutation was noted for its improved vigor and dark green, broad deltoid foliage and was subsequently isolated for further evaluation in order to confirm the distinctness and stability of the characteristics first observed. Upon confirmation of distinctness and stability, 'AMIHAW1801' was selected for commercialization.

Asexual Reproduction: Asexual reproduction of the new cultivar 'AMIHAW1801', by way of rooting leaf cuttings, was first initiated in March of 2014 at the inventor's commercial greenhouse in Heerhugowaard, the Netherlands. Through eight subsequent generations, the unique features of this cultivar have proven to be stable and true to type.

SUMMARY OF THE INVENTION

The cultivar 'AMIHAW1801' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIHAW1801'. These characteristics in combination distinguish 'AMIHAW1801' as a new and distinct *Haworthia* cultivar:

1. 'AMIHAW1801' exhibits spirally-arranged succulent foliage, held upright, in a basal rosette; and
2. 'AMIHAW1801' exhibits a fast rate of growth; and
3. 'AMIHAW1801' exhibits large, broadly deltoid foliage with prominent teeth that are moderately abundant along the proximal half of the leaf margin and become less prominent and nearly absent towards the distal portion and apex; and
4. 'AMIHAW1801' exhibits dark green foliage which is tolerant of high light levels.

BOTANICAL DESCRIPTION OF THE PLANT

Figure 1:
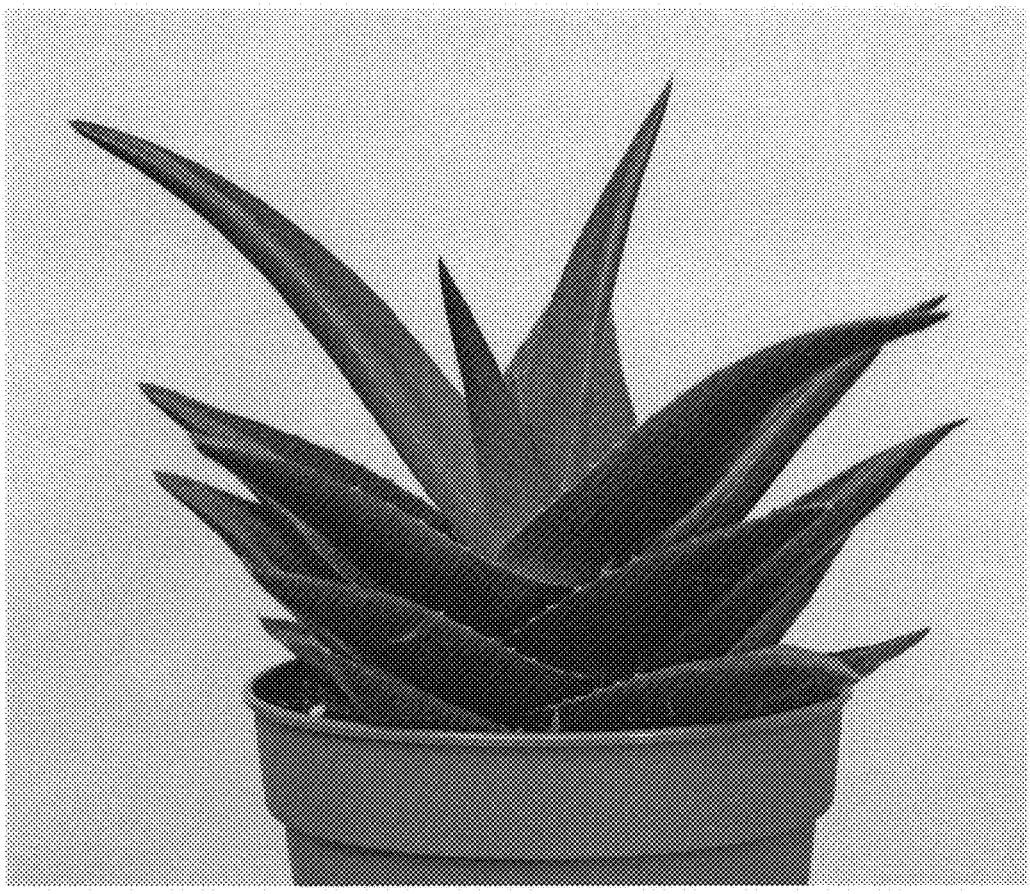
FIG. 1 illustrates, as nearly true as it is reasonably possible to make the same in color photographs of this type, an exemplary plant of 'AMIHAW1801' grown in a commercial greenhouse in Heerhugowaard, the Netherlands. This plant is approximately 7.5 months old, shown planted in a 10.5 cm container.
Figure 2:
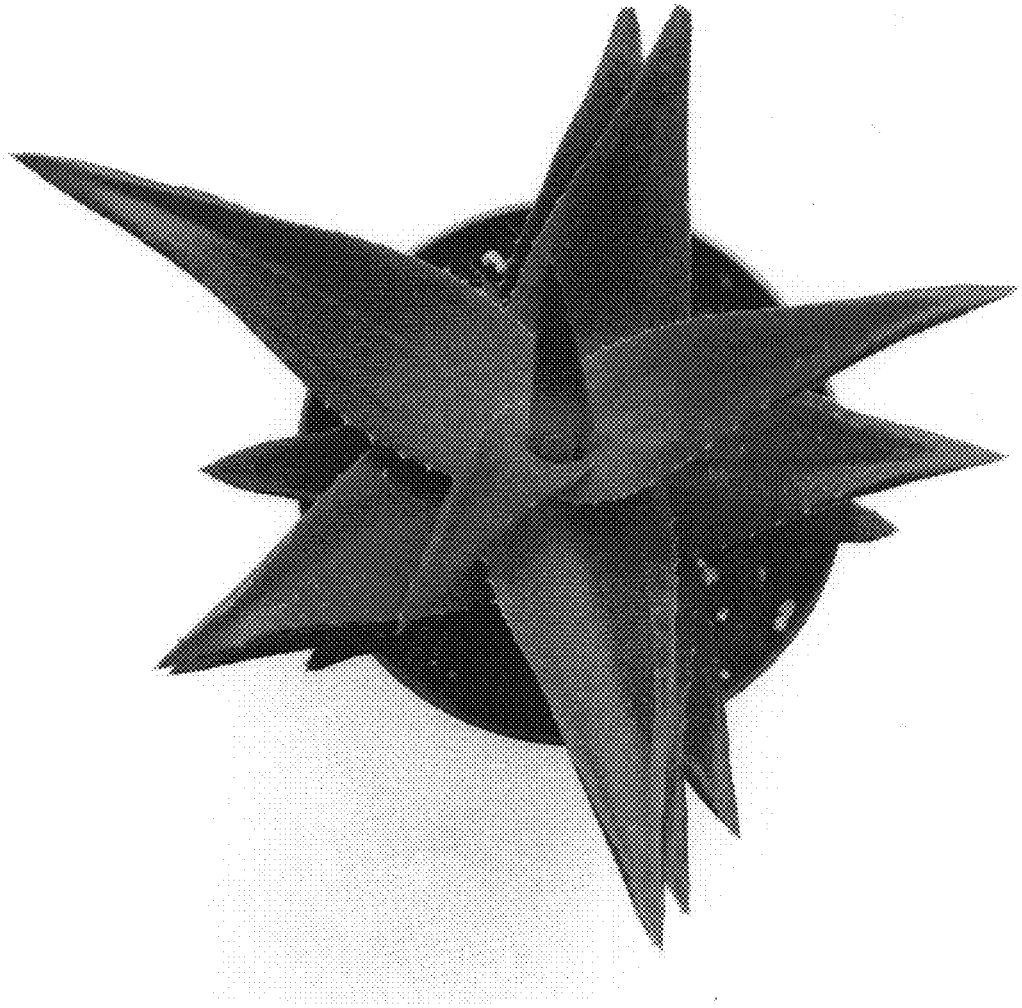
FIG. 2 illustrates, as nearly true as it is reasonably possible to make the same in color photographs of this type, the typical foliage arrangement of 'AMIHAW1801'.
Figure 3:
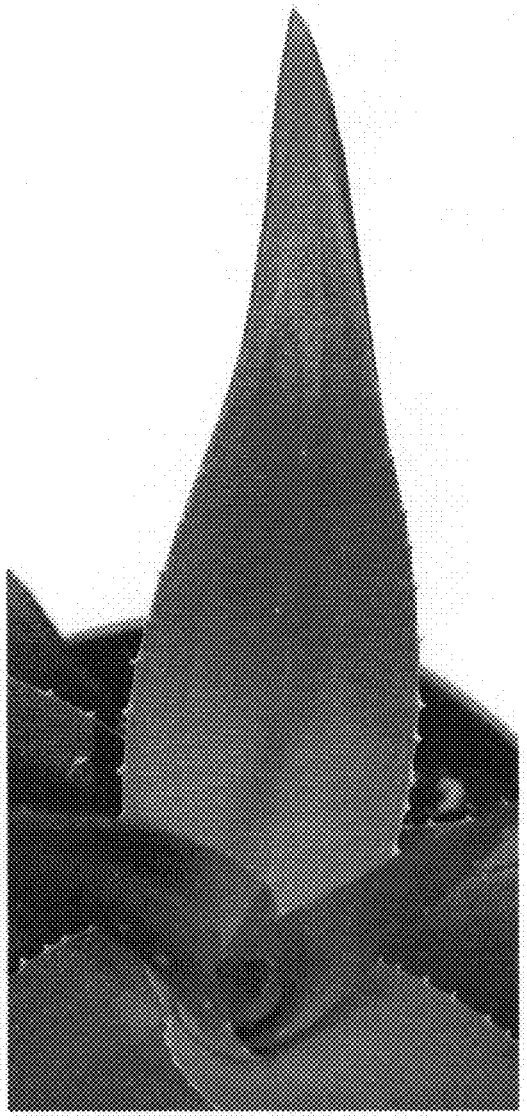
FIG. 3 illustrates, as nearly true as it is reasonably possible to make the same in color photographs of this type, the adaxial surface of the mature foliage 'AMIHAW1801'.
Figure 4:
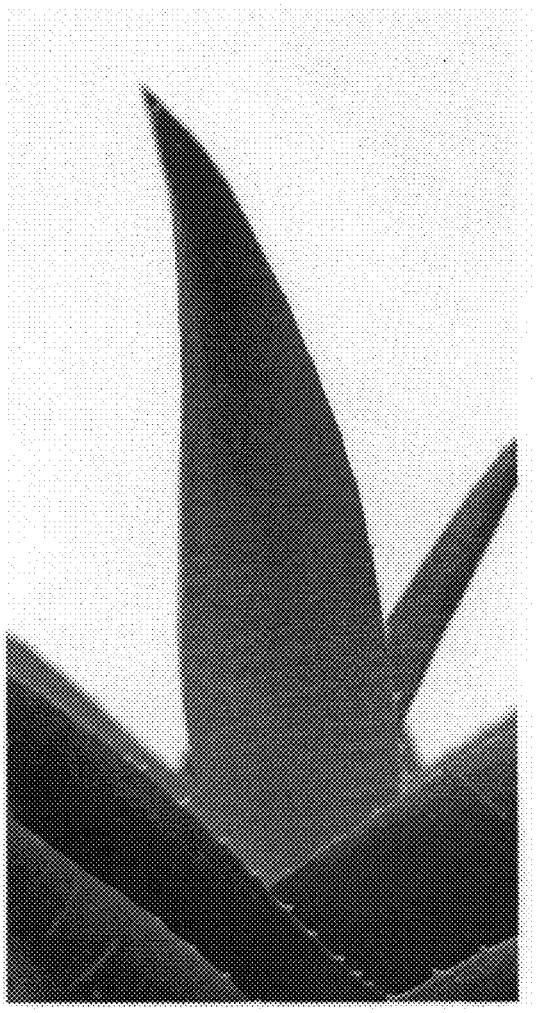
FIG. 4 illustrates, as nearly true as it is reasonably possible to make the same in color photographs of this type, the abaxial surface of the mature foliage 'AMIHAW1801'.

The following observations and measurements made in January of 2017 describe averages from a sample set of six specimens of 7.5 months old 'AMIHAW1801' plants grown in 12 cm nursery containers at commercial greenhouse in Heerhugowaard, the Netherlands. Plants were produced using conventional greenhouse production protocols for *Haworthia* plants which consisted of minimal subsurface irrigation and minimal fertilizer applications, and chemical pest and disease control measures against mealy bug, *Botrytis* sp. and *Fusarium* sp. as required. Plants were grown under approximately 50 percent shade and no photoperiodic treatments or artificial light was given to the plants.

Those skilled in the art will appreciate that certain characteristics will vary with older or, conversely, with younger plants. 'AMIHAW1801' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIHAW1801' and a comparison with the parent and closest known comparator is provided below.

Plant description:

*Growth habit*.—Succulent perennial with foliage growing in a non-branched basal rosette.

*Plant shape*.—Flattened globular.

*Height from soil level to top of foliar plane*.—12.8 cm.

*Plant spread*.—Average of 18.1 cm.

*Growth rate*.—Moderate.

*Plant vigor*.—Moderate.

*Propagation*.—Type — Leaf cuttings. Time to initiate rooting — Approximately 20 days at 18 degrees Celsius. Crop time — Approximately 30 weeks to produce a marketable plant in a 12 cm container.

*Disease and pest resistance or susceptibility*.—Neither resistance nor susceptibility to typical *Haworthia* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally arranged in a rosette.

*Division*.—Simple.

*Attachment*.—Sessile.

*Quantity*.—21 leaves per rosette.

*Shape*.—Broad deltoid.

*Dimensions*.—10.4 cm long, 4.4 cm wide, and 1.0 cm thick, on average.

*Aspect*.—Very slightly concaved and slightly curved downward at the distal portion of the leaf.

*Attitude*.—Upward to outward.

*Apex*.—Apiculate, with a soft mucronate tip.

*Base*.—Broad cuneate.

*Margin*.—Coarsely dentate with teeth that are moderately abundant along the proximal half of the leaf margin and become less prominent and nearly absent towards the distal portion and apex; teeth have an average length of 0.1 cm and are colored greyed-green, nearest to RHS 193A. Margins are not undulated or lobed.

*Texture, adaxial surface*.—Glabrous and smooth with the exception of the midrib which appears as a shallow longitudinal groove running the length of the leaf.

*Texture, abaxial surface*.—Glabrous and smooth with the exception of the midrib which appears as a shallow longitudinal groove running the length of the leaf.

*Luster, adaxial surface*.—Slightly glossy.

*Luster, abaxial surface*.—Slightly glossy.

*Color*.—Juvenile foliage, adaxial surface — Green to yellow-green, nearest to in between RHS NN137A and 147A; fading to a lighter shade of yellow-green towards the base, nearest to RHS 144A. Juvenile foliage, abaxial surface — Green, nearest to RHS NN137A, and fading to yellow-green towards the base, nearest to RHS 144B. Mature foliage, adaxial surface — Green, nearest to in between RHS NN137A and 139A, and fading to a lighter shade of green towards the base, nearest to RHS 143A. Mature foliage, abaxial surface — Green to yellow-green, nearest to in between RHS NN137A and 147A; fading to a lighter shade of green towards the base, nearest to RHS 143A.

*Venation*.—Pattern — Parallel; only the midrib is visible. Color, adaxial surface — Midrib is green, nearest to in between RHS NN137A and 139A. All other veins are not visible. Color, abaxial surface — Midrib is green to yellow-green, nearest to in between RHS NN137A and 147A. All other veins are not visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIHAW1801' differ from the parent, an unnamed *Haworthia pentagona* plant (not patented), in the following characteristics described in Table 1 below.

TABLE 1

| Characteristic | 'AMIHAW1801' | *Haworthia pentagona* parent |
|---|---|---|
| Rate of growth. | Faster than the parent. | Slower than 'AMIHAW1801'. |
| Foliage size. | Longer and broader than the parent. | Shorter and narrower than 'AMIHAW1801'. |
| General coloration of the foliage. | Darker green; remaining dark green under high light levels. | Lighter green; becoming suffused with greyed-purple to brown under high light levels. |
| Foliage margins. | Coarsely dentate with a greater abundance of larger, prominent teeth. | Entire to very lightly dentate with a fewer number of small, inconspicuous teeth. |

COMPARISONS WITH THE CLOSEST KNOWN COMPARATOR

Plants of the new cultivar 'AMIHAW1801' differ from the closest known commercial comparator, the common form of the species *Aloe mitiformis* (not patented), in the following characteristics described in Table 2 below.

TABLE 2

| Characteristic | 'AMIHAW1801' | *Aloe mitiformis* |
|---|---|---|
| Rate of growth. | Faster than *Aloe mitiformis.* | Slower than 'AMIHAW1801'. |
| General coloration of the foliage. | Darker green. | Lighter green. |
| Foliage margins. | Coarsely dentate; teeth along the margins are smaller and less abundant. | Coarsely dentate; teeth along the margins are larger and more abundant. |

That which is claimed is:

1. A new and distinct variety of *Haworthia* plant named 'AMIHAW1801', substantially as described and illustrated herein.

* * * * *